United States Patent
Peng et al.

(10) Patent No.: US 9,440,896 B2
(45) Date of Patent: Sep. 13, 2016

(54) DEHYDROCHLORINATION OF HCFC-336 ISOMERS TO 1,1,1,4,4,4-HEXAFLUORO-2-BUTYNE

(71) Applicant: THE CHEMOURS COMPANY FC LLC, Wilmington, DE (US)

(72) Inventors: Sheng Peng, Hockessin, DE (US); Mario Joseph Nappa, Newark, DE (US)

(73) Assignee: THE CHEMOURS COMPANY FC, LLC, Wilmington, DE (US)

( * ) Notice: Subject to any disclaimer, the term of this patent is extended or adjusted under 35 U.S.C. 154(b) by 0 days.

(21) Appl. No.: 14/416,313

(22) PCT Filed: Sep. 27, 2013

(86) PCT No.: PCT/US2013/062080
§ 371 (c)(1),
(2) Date: Jan. 22, 2015

(87) PCT Pub. No.: WO2014/052695
PCT Pub. Date: Apr. 3, 2014

(65) Prior Publication Data
US 2015/0203423 A1  Jul. 23, 2015

Related U.S. Application Data

(60) Provisional application No. 61/707,231, filed on Sep. 28, 2012, provisional application No. 61/716,001, filed on Oct. 19, 2012, provisional application No. 61/707,220, filed on Sep. 28, 2012.

(51) Int. Cl.
*C07C 17/25* (2006.01)

(52) U.S. Cl.
CPC .................................... *C07C 17/25* (2013.01)

(58) Field of Classification Search
CPC .............................. C07C 17/25; C07C 17/23
See application file for complete search history.

(56) References Cited

U.S. PATENT DOCUMENTS

| | | | |
|---|---|---|---|
| 7,964,759 B2 * | 6/2011 | Ishihara | ................... C07C 17/25 570/155 |
| 2010/0204529 A1 * | 8/2010 | Terada | ..................... C07C 17/23 570/160 |

FOREIGN PATENT DOCUMENTS

| | | | |
|---|---|---|---|
| JP | 2010037205 A | * | 2/2010 |
| WO | 2014052695 A1 | | 4/2014 |

OTHER PUBLICATIONS

JP 2010037205 A, Feb. 2010, pp. 1-10; English translation.*
International Search Report, PCT/US2013/062080, Mailed date Jan. Jan. 2014.
Haszeldine, The addition of free radicals to unsaturated systems. Part 1. The direction of radical addition to 3:3:3-trifluoropropene, Journal of the Chemical Society, 1952, pp. 2504-2513.
Kolomeitsev et al., Advances in trifluoromethylating phosphorus compounds, Phosphorus, Sulfur, and Silicon, vol. 109, No. 1-4, 1996, pp. 597-600.

* cited by examiner

*Primary Examiner* — Jafar Parsa
*Assistant Examiner* — Medhanit Bahta

(57) ABSTRACT

Disclosed is a process for producing hexafluoro-2-butyne comprising, reacting HCFC-336 with an aqueous solution of an alkali metal hydroxide in the presence of a quaternary alkylammonium salt which comprises at least one alkyl group of at least 8 carbons, and recovering the hexafluoro-2-butyne, wherein the conversion of dichloro-1,1,1,4,4,4-hexafluorobutane is at least 50% per hour. Also disclosed is a process for producing hexafluoro-2-butyne comprising, reacting HCFC-336 with an aqueous solution of an alkali metal hydroxide in the presence of a quaternary alkylammonium salt having alkyl groups of from four to ten carbon atoms, and mixtures thereof, and a non-ionic surfactant, and recovering the hexafluoro-2-butyne, and wherein the conversion of dichloro-1,1,1,4,4,4-hexafluorobutane to hexafluoro-2-butyne is at least 20% per hour.

13 Claims, No Drawings

DEHYDROCHLORINATION OF HCFC-336 ISOMERS TO 1,1,1,4,4,4-HEXAFLUORO-2-BUTYNE

BACKGROUND INFORMATION

1. Field of the Disclosure

This disclosure relates in general to methods of synthesis of fluorinated olefins and fluorinated alkynes.

2. Description of the Related Art

The fluorocarbon industry has been working for the past few decades to find replacement refrigerants for the ozone depleting chlorofluorocarbons (CFCs) and hydrochlorofluorocarbons (HCFCs) being phased out as a result of the Montreal Protocol. The solution for many applications has been the commercialization of hydrofluorocarbon (HFC) compounds for use as refrigerants, solvents, fire extinguishing agents, foam blowing agents and propellants. These new compounds, such as HFC refrigerants, HFC-134a and HFC-125, and blowing agents HFC-134a and 245fa being the most widely used at this time, have zero ozone depletion potential and thus are not affected by the current regulatory phase-out as a result of the Montreal Protocol.

In addition to ozone depleting concerns, global warming is another environmental concern in many of these applications. Thus, there is a need for compositions that meet both low ozone depletion standards as well as having low global warming potentials. Certain hydrofluoroolefins are believed to meet both goals. Thus there is a need for manufacturing processes that provide halogenated hydrocarbons and fluoroolefins that contain no chlorine that also have a low global warming potential. Several hydrofluoroolefins have been identified which meet these goals. One such olefin is 1,1,1,4,4,4-hexafluoro-2-butene. Efficient methods of synthesis are needed for such compounds.

SUMMARY

Disclosed is a process for producing hexafluoro-2-butyne comprising, reacting a chlorinated reactant with an aqueous solution of an alkali metal hydroxide in the presence of a phase transfer catalyst. In one embodiment, the chlorinated reactant includes a chlororfluorobutane or a chlorofluorobutene. In one embodiment, the chlorinated reactant is IHCFC-336mdd (2,3-dichloro-1,1,1,4,4,4-hexafluorobutane), HCFC-336mfa (2,2-dichloro-1,1,1,4,4,4-hexafluorobutane) or HCFO-1326mxz (E- or Z-1,1,1,4,4,4-hexafluoro-2-chloro-2-butene). As used herein, HCFC-336 is meant to include either or both of the aforementioned HCFC-336 isomers. In one embodiment, the phase transfer catalyst is a quaternary alkylammonium salt. In one embodiment, the quaternary alkylammonnium salt has at least one alkyl group of at least 8 carbons, and recovering the hexafluoro-2-butyne, wherein the conversion of dichloro-1,1,1,4,4,4-hexafluorobutane is at least 50% per hour.

Also disclosed is a process for producing hexafluoro-2-butyne comprising, reacting a chlorinated reactant with an aqueous solution of an alkali metal hydroxide in the presence of a quaternary alkylammonium salt having alkyl groups of from four to ten carbon atoms, and mixtures thereof, and a non-ionic surfactant, and recovering the hexafluoro-2-butyne, and wherein the conversion of chlorinated reactant to hexafluoro-2-butyne is at least 20% per hour The foregoing general description and the following detailed description are exemplary and explanatory only and are not restrictive of the invention, as defined in the appended claims.

DETAILED DESCRIPTION

Disclosed is a process for producing hexafluoro-2-butyne comprising, reacting a chlorinated reactant with an aqueous solution of an alkali metal hydroxide in the presence of a quaternary alkylammonium salt which comprises at least one alkyl group of at least 8 carbons, and recovering the hexafluoro-2-butyne, wherein the conversion of dichloro-1,1,1,4,4,4-hexafluorobutane is at least 50% per hour.

Also disclosed is a process for producing hexafluoro-2-butyne comprising, reacting a chlorinated reactant with an aqueous solution of an alkali metal hydroxide in the presence of a quaternary alkylammonium salt having alkyl groups of from four to ten carbon atoms, and mixtures thereof, and a non-ionic surfactant, and recovering the hexafluoro-2-butyne, and wherein the conversion of chlorinated reactant to hexafluoro-2-butyne is at least 20% per hour Many aspects and embodiments have been described above and are merely exemplary and not limiting. After reading this specification, skilled artisans appreciate that other aspects and embodiments are possible without departing from the scope of the invention.

Other features and benefits of any one or more of the embodiments will be apparent from the following detailed description, and from the claims. In addition, the individual features and elements of the embodiments disclosed herein may be used separately, in conjunction with or in combination with each other, even though described, claimed, or exemplified separately below.

As used herein, the name HCFC-336 without a designation of positional isomers, refers to either or both of HCFC-336mdd (2,3-dichloro-1,1,1,4,4,4-hexafluorobutane) or HCFC-336mfa (2,2-dichloro-1,1,1,4,4,4-hexafluorobutane). As used herein, the name HCFC-1326mxz without designation of stereochemistry refers to either or both of E- or Z-HCFC-1326mxz (E-1,1,1,4,4,4-hexafluoro-2-chloro-2-butene or Z-1,1,1,4,4,4-hexafluoro-2-chloro-2-butene).

HCFC-336 is potentially available through a number of routes, and is of interest as a potential precursor to 1,1,1,4,4,4-hexafluoro-2-butene. HCFC-336 could be prepared by hydrogenation of CFC-1316mxx, or via chlorination of HFC-356mff. Dehydrochlorination twice would provide hexafluoro-2-butyne, which could be readily hydrogenated to provide cis-1,1,1,4,4,4-hexafluoro-2-butene. While the first dehydrochlorination seemingly would be straightforward, dehydrochlorination of vinyl chlorides is classical organic chemistry to form acetylenes requires rather harsh conditions, such as very strong bases such as sodium in liquid ammonia. It has been reported that higher molecular weight polyfluorinated vinyl chlorides can be dehydrohalogenated to alkynes using aqueous base at temperatures of from 100-120° C. up to 200 or 250° C. At these temperatures however, hexafluoro-2-butyne would have too high a vapor pressure in a reactor, and be susceptible to degradation.

It has been found that either HCFC-336mdd or HCFC-336mfa can be twice dehydrochlorinated at temperatures well below 100° C. using an aqueous basic solution in combination with quaternary alkylammonium salts as a phase transfer catalyst.

As used herein, phase transfer catalyst is intended to mean a substance that facilitates the transfer of ionic compounds into an organic phase from an aqueous phase or from a solid phase. The phase transfer catalyst facilitates the reaction of these dissimilar and incompatible components. While various phase transfer catalysts may function in different ways, their mechanism of action is not determinative of their utility in the present invention provided that the phase transfer catalyst facilitates the dehydrochlorination reaction.

A phase transfer catalyst as used herein is a quaternary alkylammonium salt wherein the alkyl groups are alkyl chains having from four to ten carbon atoms. In one embodiment, the quaternary alkylammonium salt is trioctylmethylammonium chloride (Aliquat 336). The anions of the salt can be halides such as chloride or bromide, hydrogen sulfate, or any other commonly used anion.

In another embodiment, the quaternary alkylammonium salt is tetraoctylammonium chloride. In yet another embodiment, the quaternary alkylammonium salt is tetraoctylammonium hydrogen sulfate.

Other compounds commonly thought of as phase transfer catalysts in other applications, including crown ethers, cryptands or non-ionic surfactants alone, do not have a significant effect on conversion or the rate of the dehydrochlorination reaction in the same fashion.

In another embodiment, either HCFC-336mdd or HCFC-336mfa can be twice dehydrochlorinated at temperatures well below 100° C. using an aqueous basic solution in combination with quaternary alkylammonium salts wherein the alkyl groups are alkyl chains of at least four or more carbon atoms and further in combination with a non-ionic surfactant. One example of such a quaternary alkylammonium salt is tetrabutylammonium chloride.

In one embodiment, the non-ionic surfactant is an ethoxylated nonylphenol or an ethoxylated C12-C15 linear aliphatic alcohol. Suitable non-ionic surfactants include Bio-Soft® N25-9 and Makon® 10 are from Stepan Company.

In one embodiment, the quaternary alkylammonium salt is selected from the group consisting of tetrabutylammonium chloride, tetrabutylammonium bromide, tetrabutylammonium hydrogen sulfate, tetraoctylammonium chloride, tetraoctylammonium bromide, tetraoctylammonium hydrogen sulfate, methyltrioctylammonium chloride, methyltrioctylammonium bromide, tetradecylammonium chloride, tetradecylammonium bromide, and tetradodecylammonium chloride.

Dehydrochlorination of HCFC-336 can be effected with quaternary alkylammonium salts, wherein the alkyl groups are alkyl chains having at least one alkyl chain of 8 carbons or more. In another embodiment, the quaternary alkylammonium salt has three alkyl chains of 8 carbons or more, such as trioctylmethylammonium salt. In yet another embodiment, the quaternary alkylammonium salt is a tetraoctylammonumium salt. The anions of the salt can be halides such as chloride or bromide, hydrogen sulfate, or any other commonly used anion.

In one embodiment, the quaternary alkylammonium salts is added in an amount of from 0.5 mole percent to 2.0 mole percent of the HCFC-336. In another embodiment, the quaternary alkylammonium salts is added in an amount of from 1 mole percent to 2 mole percent of the HCFC-336. In yet another embodiment, the quaternary alkylammonium salts is added in an amount of from 1 mole percent to 1.5 mole percent of the HCFC-336. In one embodiment, the quaternary alkylammonium salt is added in an amount of from 1 mole percent to 1.5 mole percent of the HCFC-336 and the weight of non-ionic surfactant added is from 1.0 to 2.0 times the weight of the quaternary alkylammonium salt.

In one embodiment, the reaction is conducted at a temperature of from about 60 to 90° C. In another embodiment, the reaction is conducted at 70° C.

As used herein, the basic aqueous solution is a liquid (whether a solution, dispersion, emulsion, or suspension and the like) that is primarily an aqueous liquid having a pH of over 7. In some embodiments the basic aqueous solution has a pH of over 8. In some embodiments, the basic aqueous solution has a pH of over 10. In some embodiments, the basic aqueous solution has a pH of 10-13. In some embodiments, the basic aqueous solution contains small amounts of organic liquids which may be miscible or immiscible with water. In some embodiments, the liquid medium in the basic aqueous solution is at least 90% water. In one embodiment the water is tap water; in other embodiments the water is deionized or distilled.

The base in the aqueous basic solution is selected from the group consisting of hydroxide, oxide, carbonate, or phosphate salts of alkali, alkaline earth metals and mixtures thereof. In one embodiment, bases which may be used lithium hydroxide, sodium hydroxide, potassium hydroxide, calcium hydroxide, magnesium oxide, calcium oxide, sodium carbonate, potassium carbonate, sodium phosphate, potassium phosphate, or mixtures thereof.

Hydrofluorochloroolefin HCFC-1326mxz is an impurity in some schemes for the synthesis of 1,1,1,4,4,4-hexafluoro-2-butene, which is of interest as a foam expansion agent. In other potential schemes, it can be an intermediate. One method of synthesis of HCFC-1326mxz is through the hydrogenation of 1,1,1,4,4,4-hexafluoro-2,3-dichloro-2-butene. Whatever the method of synthesis, one typically obtains a mixture of the Z- and E-stereoisomers about the double bond. Unfortunately, it exhibits rather high toxicity, so whether formed as an impurity, or as an intermediate, it is desirable to convert it into useful product in high yield. Dehydrochlorination would provide hexafluoro-2-butyne, which could be hydrogenated to provide 1,1,1,4,4,4-hexafluoro-2-butene. In classical organic chemistry, the dehydrochlorination of vinyl chlorides to form acetylenes requires rather harsh conditions, such as very strong bases, such as sodium in liquid ammonia. It has been reported that higher molecular weight polyfluorinated vinyl chlorides can be dehydrohalogenated to alkynes using aqueous base at temperatures of from 100-120° C. up to 200 or 250° C. At these temperatures however, hexafluoro-2-butyne would have too high a vapor pressure in a reactor, and be susceptible to degradation.

It has been found that Z- and E-1,1,1,4,4,4-hexafluoro-2-chloro-2-butene can be dehydrochlorinated at temperatures well below 100° C. using an aqueous basic solution in combination with quaternary alkylammonium salts as a phase transfer catalyst.

As used herein, phase transfer catalyst is intended to mean a substance that facilitates the transfer of ionic compounds into an organic phase from an aqueous phase or from a solid phase. The phase transfer catalyst facilitates the reaction of these dissimilar and incompatible components. While various phase transfer catalysts may function in different ways, their mechanism of action is not determinative of their utility in the present invention provided that the phase transfer catalyst facilitates the dehydrochlorination reaction.

A phase transfer catalyst as used herein is a quaternary alkylammonium salt wherein the alkyl groups are alkyl chains having from four to twelve carbon atoms. In one embodiment, the quaternary alkyl ammonium salt is a tetrabutylammonium salt. The anions of the salt can be halides such as chloride or bromide, hydrogen sulfate, or any other commonly used anion.

In another embodiment, the quaternary alkylammonium salt is trioctylmethylammonium chloride (Aliquat 336). In another embodiment, the quaternary alkylammonium salt is tetraoctylammonium chloride. In yet another embodiment, the quaternary alkylammonium salt is tetraoctylammonium hydrogen sulfate.

Other compounds commonly thought of as phase transfer catalysts in other applications, including crown ethers, cryptands or non-ionic surfactants alone, do not have a significant effect on conversion or the rate of the dehydrochlorination reaction in the same fashion.

The Z- and E-isomers of 1,1,1,4,4,4-hexafluoro-2-chloro-2-butene exhibit significantly different reactivities with respect to dehydrochlorination, and have different requirements for what functions as an effective phase transfer catalyst in this reaction. Dehydrochlorination of the Z-isomer

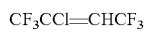
$CF_3CCl=CHCF_3$ can be effected with quaternary alkylammonium salts wherein the alkyl groups are alkyl chains having from four to twelve carbon atoms. The anions of the salt can be halides such as chloride or bromide, hydrogen sulfate, or any other commonly used anion. In one embodiment, the quaternary alkyl ammonium salt is a tetrabutylammonium salt. In another embodiment, the quaternary alkylammonium salt is a tetrahexylammonium salt. In another embodiment, the quaternary alkylammonium salt is a tetraoctylammonumium salt. In yet another embodiment, the quaternary alkylammonium salt is a trioctylmethylammonumium salt.

Dehydrochlorination of the E-isomer of 1,1,1,4,4,4-hexafluoro-2-chloro-2-butene can be effected with quaternary alkylammonium salts, wherein the alkyl groups are alkyl chains having at least one alkyl chain of 8 carbons or more. In another embodiment, the quaternary alkylammonium salt has three alkyl chains of 8 carbons or more, such as trioctylmethylammonium salt. In yet another embodiment, the quaternary alkylammonium salt is a tetraoctylammonumium salt. In yet another embodiment, the quaternary ammonium salt is a tetradecylammonium salt. In yet another embodiment, the quaternary alkylammonium salt is a tetradodecylammonium salt. The anions of the salt can be halides such as chloride or bromide, hydrogen sulfate, or any other commonly used anion.

In yet another embodiment, dehydrochlorination of the E-isomer of 1,1,1,4,4,4-hexafluoro-2-chloro-2-butene can be effected with quaternary alkylammonium salts, wherein the alkyl groups are alkyl chains having from four to twelve carbon atoms, and in the presence of a non-ionic surfactant. The non-ionic surfactants can be ethoxylated nonylphenols, and ethoxylated C12 to C15 linear aliphatic alcohols. Suitable non-ionic surfactants include Bio-Soft® N25-9 and Makon® 10 are from Stepan Company.

In one embodiment, the quaternary alkylammonium salts is added in an amount of from 0.5 mole percent to 2.0 mole percent of the 1,1,1,4,4,4-hexafluoro-2-chloro-2-butene. In another embodiment, the quaternary alkylammonium salts is added in an amount of from 1 mole percent to 2 mole percent of the 1,1,1,4,4,4-hexafluoro-2-chloro-2-butene. In yet another embodiment, the quaternary alkylammonium salts is added in an amount of from 1 mole percent to 1.5 mole percent of the 1,1,1,4,4,4-hexafluoro-2-chloro-2-butene.

In one embodiment, the dehydrochlorination of Z- or E-1,1,1,4,4,4-hexafluoro-2-chloro-2-butene is conducted in the presence of an alkali metal halide salt. In one embodiment, the alkali metal is sodium or potassium. In one embodiment, the halide is chloride or bromide. In one embodiment, the alkali metal halide salt is sodium chloride. Without wishing to be bound by any particular theory, it is believed that the alkali metal halide salt stabilizes the phase transfer catalyst. Although the dehydrochlorination reaction itself produces alkali metal chloride, and in particular sodium chloride if sodium hydroxide is used as the base, addition of extra sodium chloride provides a further effect of increasing the yield of hexafluoro-2-butyne.

Addition of alkali metal halide salt also reduces the amount of fluoride ion measured in the water effluent from the reaction. Without wishing to be bound by any particular theory, the presence of fluoride is believed to result from decomposition of either the 1,1,1,4,4,4-hexafluoro-2-chloro-2-butene starting material, or the hexafluoro-2-butyne product.

In several samples, the amount of fluoride ion found in the water effluent from the dehydrochlorination is about 6000 ppm. In several examples, using from 30 to 60 equivalents of sodium chloride per mole of phase transfer catalyst, the amount of fluoride ion in the water effluent is reduced to 2000 ppm. In one embodiment, the alkali metal halide is added at from 25 to 100 equivalents per mole of phase transfer catalyst. In another embodiment, the alkali metal halide is added at from 30 to 75 equivalents per mole of phase transfer catalyst. In yet another embodiment, the alkali metal halide is added at from 40 to 60 equivalents per mole of phase transfer catalyst.

In one embodiment, the reaction is conducted at a temperature of from about 60 to 90° C. In another embodiment, the reaction is conducted at 70° C.

As used herein, the basic aqueous solution is a liquid (whether a solution, dispersion, emulsion, or suspension and the like) that is primarily an aqueous liquid having a pH of over 7. In some embodiments the basic aqueous solution has a pH of over 8. In some embodiments, the basic aqueous solution has a pH of over 10. In some embodiments, the basic aqueous solution has a pH of 10-13. In some embodiments, the basic aqueous solution contains small amounts of organic liquids which may be miscible or immiscible with water. In some embodiments, the liquid medium in the basic aqueous solution is at least 90% water. In one embodiment the water is tap water; in other embodiments the water is deionized or distilled.

The base in the aqueous basic solution is selected from the group consisting of hydroxide, oxide, carbonate, or phosphate salts of alkali, alkaline earth metals and mixtures thereof. In one embodiment, bases which may be used lithium hydroxide, sodium hydroxide, potassium hydroxide, calcium hydroxide, magnesium oxide, calcium oxide, sodium carbonate, potassium carbonate, sodium phosphate, potassium phosphate, or mixtures thereof.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. In case of conflict, the present specification, including definitions, will control. In addition, the materials, methods, and examples are illustrative only and not intended to be limiting.

EXAMPLES

The concepts described herein will be further described in the following examples, which do not limit the scope of the invention described in the claims.

Tetra-n-butylammonium bromide (TBAB), Tetra-n-butylammonium hydrogen sulfate, Trioctylmethylammonium chloride (Aliquat® 336), Tetraoctylammonium chloride (TOAC) Tetraoctylammonium hydrogensulfate (TOAHS) and Tributylmethylammonium bromide (TBMAB) are available from Sigma Aldrich, St. Louis, Mo. Bio-Soft® N25-9 and Makon® 10 are from Stepan Company, Northfield, Ill.; 1326 is available from Synquest Labs, Inc.

Legend
HCFC-336mfa is $CF_3CCl_2CH_2CF_3$
HCFC-336mdd is $CF_3CHClCHClCF_3$
HCFC-1326mxy is $CF_3CCl\!=\!CHCF_3$
HFB is $CF_3C\!\equiv\!CCF_3$ Example 1

Example 1 demonstrates the conversion of 336mdd to hexafluorobutyne in the presence of Aliquat 336.

NaOH aqueous solution (22 mL, 0.22 mol) was added to the 336mdd (23.5 g, 0.1 mol) and water (5.6 mL) in the presence of Aliquat® 336 (0.53 g, 0.001325 mol) at room temperature. The reaction temperature was raised to 70° C. after the addition, and gas chromatography was used to monitor the reaction. The reaction was completed after 2 hour and 14 g product (conversion: 100%; yield: 86%) was collected in a dry ice trap.

Example 2

Example 2 demonstrates the conversion of 336mfa to hexafluoro-2-butyne in the presence of Aliquat 336.

NaOH aqueous solution (22 mL, 0.22 mol) is added to the 336mfa (23.5 g, 0.1 mol) and water (5.6 mL) in the presence of Aliquat® 336 (0.53 g, 0.001325 mol) at room temperature. The reaction temperature is raised to 70° C. after the addition, and gas chromatography is used to monitor the reaction. The reaction is completed after 2 hour and the hexafluorobutyne is collected in a dry ice trap.

Example 3

Example 3 demonstrates the conversion of 336mfa to hexafluoro-2-butyne in the presence of tetrabutylammonium chloride and non-ionic surfactant.

NaOH aqueous solution (22 mL, 0.22 mol) is added to the 336mfa (23.5 g, 0.1 mol) and water (5.6 mL) in the presence of tetrabutylammonium bromide (0.45 g, 0.001325 mol) and Makon® 10 (0.7 g) at room temperature. The reaction temperature is raised to 70° C. after the addition, and gas chromatography is used to monitor the reaction. The reaction is completed after 4.5 hours and the hexafluorobutyne is collected in a dry ice trap.

Comparative Example 1

NaOH aqueous solution (23 mL, 0.23 mol) is added to the mixture of HCFC-336mfa (23.5 g, 0.1 mol) and water (18 mL) at 37° C. The reaction temperature is raised to 70° C. after the addition, and gas chromatography was used to monitor the reaction. After thirty one hours. 0.36 g hexafluoro-2-butyne (conversion: 2.2%; yield: 2.2%) was collected in a dry ice trap.

Comparative Example 2

NaOH aqueous solution (10 mL, 0.10 mol) is added to the mixture of HCFC-336mfa (11.8 g, 0.05 mol) and water (18 mL) at 37° C. in the presence of 15-Crown-5 (0.65 g, 0.003 mol). The reaction temperature is raised to 70° C. after the addition, and gas chromatography is used to monitor the reaction. The reaction is not completed after thirty hours. 1.16 g hexafluoro-2-butyne (conversion: 14%; yield: 14%) is collected in a dry ice trap.

Comparative Example 3

NaOH aqueous solution (22 mL, 0.22 mol) is added to the HCFC-336mfa (23 g, 0.1 mol) and water (18 mL) at 37° C. in the presence of Makon® 10 (0.7 g). The reaction temperature is raised to 70° C. after the addition, and gas chromatography is used to monitor the reaction. The reaction is not completed after twenty two hours. 1.09 g hexafluoro-2-butyne (conversion: 17%; yield: 6.8%) was collected in a dry ice trap.

Example 4

NaOH aqueous solution (12 mL, 0.12 mol) was added to the mixture of Z-1326 (20 g, 0.1 mol) and water (18 mL) in the presence of Tetra-n-butylammonium bromide (0.45 g, 0.001325 mol) at 35° C. The reaction temperature was raised to 70° C. after the addition, and gas chromatography was used to monitor the reaction. The reaction was completed after 1 hour and 15.4 g product (conversion: 100%; yield: 95%) was collected in a dry ice trap.

Example 5

NaOH aqueous solution (12 mL, 0.12 mol) was added to the mixture of Z-1326 (20 g, 0.1 mol) and water (18 mL) in the presence of Tetra-n-butylammonium hydrogensulfate (0.43 g, 0.001325 mol) at 35° C. The reaction temperature was raised to 70° C. after the addition, and gas chromatography was used to monitor the reaction. The reaction was completed after 1 hour and 11 product (conversion: 100%; yield: 71%) was collected in a dry ice trap.

Example 6

NaOH aqueous solution (12 mL, 0.12 mol) was added to the mixture of Z-1326 (20 g, 0.1 mol) and water (18 mL) in the presence of Aliquat® 336 (0.53 g, 0.001325 mol) at 35° C. The reaction temperature was raised to 70° C. after the addition, and gas chromatography was used to monitor the reaction. The reaction was completed after 1 hour and 15.6 g product (conversion: 100%; yield: 96%) was collected in a dry ice trap.

Example 7

NaOH aqueous solution (12 mL, 0.12 mol) was added to the mixture of E-1326 (20 g, 0.1 mol) and water (18 mL) in the presence of Aliquat® 336 (0.53 g, 0.001325 mol) at 42° C. The reaction temperature was raised to 70° C. after the addition, and gas chromatography was used to monitor the reaction. The reaction was completed after 1 hours and 15.8 g product (conversion: 100%; yield: 98%) was collected in a dry ice trap.

Example 8

NaOH aqueous solution (12 mL, 0.12 mol) was added to the mixture of E-1326 (20 g, 0.1 mol) and water (18 mL) in the presence of Tetra-n-butylammonium bromide (0.45 g, 0.001325 mol) at 42° C. The reaction temperature was raised to 70° C. after the addition, and gas chromatography was used to monitor the reaction. The reaction was not completed after seven hours. 12.6 g product (conversion: 78%; yield: 78%) was collected in a dry ice trap.

Example 9

NaOH aqueous solution (12 mL, 0.12 mol) was added to the mixture of E-1326 (20 g, 0.1 mol) and water (18 mL) in the presence of Tetra-n-butylammonium hydrogen sulfate (0.43 g, 0.001325 mol) at 42° C. The reaction temperature was raised to 70° C. after the addition, and gas chromatography was used to monitor the reaction. The reaction was not completed after seven hours. 12.6 g product (conversion: 77%; yield: 77%) was collected in a dry ice trap.

Example 10

NaOH aqueous solution (12 mL, 0.12 mol) was added to the mixture of E-1326 (20 g, 0.1 mol) and water (18 mL) in the presence of Tetraoctylammonium bromide (0.72 g, 0.001325 mol) at 42° C. The reaction temperature was raised to 70° C. after the addition, and gas chromatography was used to monitor the reaction. The reaction was completed after six and half hours. 15.6 g product (conversion: 100%; yield: 95%) was collected in a dry ice trap.

Example 11

NaOH aqueous solution (12 mL, 0.12 mol) was added to the mixture of E-1326 (20 g, 0.1 mol) and water (18 mL) in the presence of Tetraoctylammonium chloride (0.43 g, 0.001325 mol) at 42° C. The reaction temperature was raised to 70° C. after the addition, and gas chromatography was used to monitor the reaction. After five and half hours, 15.2 g product (conversion: 95%; yield: 93%) was collected in a dry ice trap.

Example 12

NaOH aqueous solution (12 mL, 0.12 mol) was added to the mixture of E-1326 (20 g, 0.1 mol) and water (18 mL) in the presence of Tetra-n-butylammonium chloride (0.37 g, 0.001325 mol) at 42° C. The reaction temperature was raised to 70° C. after the addition, and gas chromatography was used to monitor the reaction. After twenty three hours, 14.8 g product (conversion: 90%; yield: 87%) was collected in a dry ice trap.

Example 13

NaOH aqueous solution (12 mL, 0.12 mol) was added to the mixture of E-1326 (20 g, 0.1 mol) and water (18 mL) in the presence of tributylmethylammonium chloride (0.31 g, 0.001325 mol) at 42° C. The reaction temperature was raised to 70° C. after the addition, and gas chromatography was used to monitor the reaction. After twenty three hours, 8 g product (conversion: 59%; yield: 49%) was collected in a dry ice trap.

Example 14

NaOH aqueous solution (12 mL, 0.12 mol) was added to the mixture of ZE-1326 (20 g, 0.1 mol) and water (18 mL) in the presence of Tetrabutylammonium bromide (0.45 g, 0.001325 mol) and Bio-Soft® N25-9 (0.7 g) at 38° C. The reaction temperature was raised to 70° C. after the addition, and gas chromatography was used to monitor the reaction. The reaction was completed after 5 hours. 13 g product (conversion: 100%; yield: 80%) was collected in a dry ice trap.

Example 15

NaOH aqueous solution (12 mL, 0.12 mol) was added to the mixture of ZE-1326 (20 g, 0.1 mol) and water (18 mL) in the presence of Tetrabutylammonium bromide (0.45 g, 0.001325 mol) and Makon® 10 (0.7 g) at 38° C. The reaction temperature was raised to 70° C. after the addition, and gas chromatography was used to monitor the reaction. The reaction was completed after 5 hours. 11.2 g product (conversion: 100%; yield: 69%) was collected in a dry ice trap.

Example 16

10 M NaOH aqueous solution (12 mL, 0.12 mol) was added over 30 min to a ZE-1326 (20 g, 0.1 mol) and water (18 mL) in the presence of NaCl (2.3 g, 0.0393 mol) and Aliquat® 336 (0.53 g, 0.001325 mol) at 37° C. When the addition was complete, the reaction temperature was raised to 70° C. after the addition, and gas chromatography was used to monitor the reaction. The reaction was completed after 1 hour and 20 minutes and the water layer was submitted for wt % fluoride analysis.

Example 17

NaOH aqueous solution (12 mL, 0.12 mol) was added over 30 min to a ZE-1326 (20 g, 0.1 mol) and water (18 mL) in the presence of NaCl (4.6 g, 0.0786 mol) and Aliquat® 336 (0.53 g, 0.001325 mol) at 37° C. When the addition was complete, the reaction temperature was raised to 70° C. after the addition, and gas chromatography was used to monitor the reaction. The reaction was completed after 1 hour and 20 minutes and the water layer was submitted for wt % fluoride analysis.

Example 18

NaOH aqueous solution (12 mL, 0.12 mol) was added over 30 min to a mixture of ZE-1326 (20 g, 0.1 mol) and water (18 mL) in the presence of NaCl (3.45 g, 0.0590 mol) and Aliquat® 336 (0.53 g, 0.001325 mol) at 37° C. When the addition was complete, the reaction temperature was raised to 70° C. after the addition, and gas chromatography was used to monitor the reaction. The reaction was completed after 2 hours and the water layer was submitted for wt % fluoride analysis.

Comparative Example 4

NaOH aqueous solution (12 mL, 0.12 mol) was added to the mixture of ZE-1326 (20 g, 0.1 mol) and water (18 mL) at 37° C. The reaction temperature was raised to 70° C. after the addition, and gas chromatography was used to monitor the reaction. After thirty one hours. 0.36 g product (conversion: 2.2%; yield: 2.2%) was collected in a dry ice trap.

Comparative Example 5

NaOH aqueous solution (6 mL, 0.06 mol) was added to the mixture of ZE-1326 (10 g, 0.05 mol) and water (18 mL) at 37° C. in the presence of 15-Crown-5 (0.65 g, 0.003 mol). The reaction temperature was raised to 70° C. after the addition, and gas chromatography was used to monitor the reaction. The reaction was not completed after thirty hours. 1.16 g product (conversion: 14%; yield: 14%) was collected in a dry ice trap.

Comparative Example 6

NaOH aqueous solution (12 mL, 0.12 mol) was added to the mixture of ZE-1326 (20 g, 0.1 mol) and water (18 mL) at 37° C. in the presence of Makon® 10 (0.7 g). The reaction temperature was raised to 70° C. after the addition, and gas chromatography was used to monitor the reaction. The reaction was not completed after twenty two hours. 1.09 g product (conversion: 17%; yield: 6.8%) was collected in a dry ice trap.

TABLE 1

| Examples | 1326 | Base | PTC | Time (hr) | Conversion (%) | Yield (%) |
|---|---|---|---|---|---|---|
| 4 | Z | NaOH | TBAB | 1 | 100 | 95 |
| 5 | Z | NaOH | TBAHS | 1 | 100 | 71 |
| 6 | Z | NaOH | Aliquat ® 336 | 1 | 100 | 96 |
| 7 | E | NaOH | Aliquat ® 336 | 1 | 100 | 98 |
| 8 | E | NaOH | TBAB | 7 | 78 | 78 |
| 9 | E | NaOH | TBAHS | 7 | 77 | 77 |
| 10 | E | NaOH | TOAB | 6.5 | 100 | 95 |
| 11 | E | NaOH | TOACI | 5.5 | 95 | 17.3 |
| 12 | E | NaOH | TBACI | 23 | 90 | 93 |
| 13 | E | NaOH | TBMACI | 23 | 59 | 87 |
| 14 | ZE | NaOH | TBAB + Biosoft 25-9 | 5 | 100 | 49 |
| 15 | ZE | NaOH | TBAB + Makon 10 | 5 | 100 | 69 |
| 16 | ZE | NaOH | Aliquat ® 336 | 1.3 | 100 | |
| 17 | ZE | NaOH | Aliquat ® 336 | 1.3 | 100 | |
| 18 | ZE | NaOH | Aliquat ® 336 | 2 | 100 | |
| Comp 4 | ZE | NaOH | None | 31 | 2.2 | 2.2 |
| Comp. 5 | ZE | NaOH | 15-Crown-5 | 30 | 14 | 14 |
| Comp. 6 | ZE | NaOH | Makon 10 | 22 | 17 | 6.8 |

* 1326 was added to KOH

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, reference to values stated in ranges include each and every value within that range.

What is claimed is:

1. A process for producing hexafluoro-2-butyne comprising reacting Z-1,1,1,4,4,4-hexafluoro-2-chloro-2-butene with an aqueous solution of an alkali metal hydroxide comprising an alkali metal halide in the presence of a quaternary alkylammonium salt having alkyl groups of from four to twelve carbon atoms and mixtures thereof, to produce a mixture comprising hexafluoro-2-butyne, and recovering the hexafluoro-2-butyne, wherein the conversion of Z-1,1,1,4,4,4-hexafluoro-2-chloro-2-butene to hexafluoro-2-butyne is at least 50% per hour, wherein said reaction occurs at less than 100° C.

2. The process according to claim 1, wherein said alkali metal halide is sodium chloride.

3. The process according to claim 1 wherein the aqueous solution is made from a base selected from the group consisting of lithium hydroxide, sodium hydroxide, potassium hydroxide, calcium hydroxide, magnesium oxide, calcium oxide, sodium carbonate, potassium carbonate, sodium phosphate, potassium phosphate, and mixtures thereof.

4. The process according to claim 1, wherein the aqueous solution is made from sodium hydroxide or potassium hydroxide.

5. A process for producing hexafluoro-2-butyne comprising, reacting a fluorochloroolefin comprising E-1,1,1,4,4,4-hexafluoro-2-chloro-2-butene with an aqueous solution of an alkali metal hydroxide in the presence of a quaternary alkylammonium salt which comprises at least one alkyl group of at least 8 carbons, and recovering the hexafluoro-2-butyne, wherein the conversion of E-1,1,1,4,4,4-hexafluoro-2-chloro-2-butene to hexafluoro-2-butyne is at least 15% per hour, wherein said reaction occurs at less than 100° C.

6. The process according to claim 5, wherein said alkali metal hydroxide further comprises an alkali metal halide.

7. The process according to claim 6, wherein said alkali metal halide is sodium chloride.

8. The process according to claim 5, wherein said quaternary alkylammonium salt has at least 3 alkyl groups of eight carbons or higher.

9. The process according to claim 5, wherein said quaternary alkylammounium salt is methyltrioctylammonium chloride.

10. The process according to claim 9, wherein the conversion of E-1,1,1,4,4,4-hexafluoro-2-chloro-2-butene to hexafluoro-2-butyne is at least 50% per hour.

11. The process according to claim 5 wherein the aqueous solution is made from a base selected from the group consisting of lithium hydroxide, sodium hydroxide, potassium hydroxide, calcium hydroxide, magnesium oxide, calcium oxide, sodium carbonate, potassium carbonate, sodium phosphate, potassium phosphate, and mixtures thereof.

12. The process according to claim 5, wherein the aqueous solution is made from sodium hydroxide or potassium hydroxide.

13. The process according to claim 5, wherein said fluorochloroolefin further comprises Z-1,1,1,4,4,4-hexafluoro-2-chloro-2-butene.

* * * * *